United States Patent
Cerovsky et al.

(10) Patent No.: US 10,160,785 B2
(45) Date of Patent: Dec. 25, 2018

(54) ANTIMICROBIAL PEPTIDES AND THEIR USE FOR THE TREATMENT OF TOPICAL INFECTIONS

(71) Applicants: USTAV ORGANICKE CHEMIE A BIOCHEMIE AV CR, V.V.I., Prague (CZ); FYZIOLOGICKY USTAV AV CR, V.V.I., Prague (CZ)

(72) Inventors: Vaclav Cerovsky, Roztoky (CZ); Ondrej Nesuta, Opava (CZ); Vlasta Dudkova, Prague (CZ); Hana Sychrova, Prague (CZ); Marie Kodedova, Nehvizdy (CZ)

(73) Assignees: USTAV ORGANICKE CHEMIE A BIOCHEMIE AV CR, V.V.I., Prague (CZ); FYZIOLOGICKY USTAV AV CR, V.V.I., Prague (CZ)

( * ) Notice: Subject to any disclaimer, the term of this patent is extended or adjusted under 35 U.S.C. 154(b) by 0 days.

(21) Appl. No.: 15/564,035

(22) PCT Filed: Apr. 8, 2016

(86) PCT No.: PCT/CZ2016/050009
§ 371 (c)(1),
(2) Date: Oct. 3, 2017

(87) PCT Pub. No.: WO2016/161997
PCT Pub. Date: Oct. 13, 2016

(65) Prior Publication Data
US 2018/0086792 A1 Mar. 29, 2018

(30) Foreign Application Priority Data
Apr. 10, 2015 (CZ) ................................ PV2015-244

(51) Int. Cl.
*C07K 7/08* (2006.01)
*A61K 38/00* (2006.01)
*A61K 38/04* (2006.01)
*A61K 38/10* (2006.01)

(52) U.S. Cl.
CPC ................ *C07K 7/08* (2013.01); *A61K 38/04* (2013.01); *A61K 38/00* (2013.01); *A61K 38/10* (2013.01)

(58) Field of Classification Search
None
See application file for complete search history.

(56) References Cited

PUBLICATIONS

Cujova, S., et al., "Interaction of a novel antimicrobial peptide isolated from the venom of solitary bee Colletes daviesanus with phospholipid vesiles and *Escherichia coli* cells", Journal of Peptide Science, vol. 20, Aug. 14, 2014 (Aug. 14, 2014), pp. 885-895, XP002758497, John Wiley and Sons Ltd., ISSN: 1075-2617 the whole document.

Nesuta, O, et al., "Antimicrobial peptide from the wild bee Hylaeus signatus venom and its analogues: structure-activity study and synergistic effect with antibiotics", Journal of Natural Products., vol. 79, No. 4, Mar. 21, 2016 (Mar. 21, 2016), pp. 1073-1083, XP002758498, American Chemical Society ISSN: 0163-3864 the whole document.

International Search Report and Written Opinion of corresponding PCT application No. PCT/CZ2016/050009, dated Jun. 20, 2016.

*Primary Examiner* — Christina Bradley
(74) *Attorney, Agent, or Firm* — Notaro, Michalos & Zaccaria P.C.

(57) ABSTRACT

Synthetic analogs of general formula (I-A),

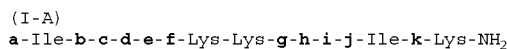

(I-A)
a-Ile-b-c-d-e-f-Lys-Lys-g-h-i-j-Ile-k-Lys-NH₂ where a is Gly, Lys or β-Ala; b is Met, Leu, Nle, Ile, Trp, Val or Phe; c is Ser, Lys, Arg or Orn; d is Ser, Lys, Arg or Orn; e is Leu, Nle, Ile, Trp, Val or Phe; f is Met, Leu, Nle, Ile, Trp, Val or Phe; g is Leu, Nle, Ile or Trp; h is Lys, Arg, Orn or Ala; i is Lys, Arg, Orn or Ala; j is Ile, Leu, Nle or His; k is Lys, Arg, Orn or Ala; where amino acids in all positions may be in D-configuration, and their use for the treatment of topical infections caused by pathogenic bacteria or yeasts.

9 Claims, 1 Drawing Sheet
Specification includes a Sequence Listing.

ANTIMICROBIAL PEPTIDES AND THEIR USE FOR THE TREATMENT OF TOPICAL INFECTIONS

FIELD OF ART

The invention involves peptides of the general formula (I-A) and their application for the treatment of infection diseases caused by various pathogenic bacteria and by the yeasts of *Candida* strains. These are mostly topical infections such as difficult-to-heal wounds, skin disorders, mucosal infections, as well as infections of catheters, artificial joints and implanted materials. They are commonly accompanied by the occurrence of microbial biofilms.

BACKGROUND ART

Infection causes serious complications during the healing process of acute and chronic wounds. Formation of biofilm contributes to the chronicity of early infections [Rulík et al., 2011] which leads to the chronic inflammation of the wound scum thus preventing the wound healing and promoting the dissemination of the infection [Bjarnsholt, 2013].

Biofilms are agglomerates of microorganisms adhered to a wound scum or to the surfaces of the artificial implants such as joint implants, osteosynthesis materials, cement fixations or catheters inserted into the body of patient. Biofilm is also formed in connection with dental plaque, urinary tract infections, eye infections and infections of ear canal or middle ear. It is estimated that biofilm-related infections account for at least 80% of all human infections. Microorganisms living in biofilms are embedded in a matrix of extracellular polymer substances made of polysaccharides, alginates and other compounds [Bjarnsholt et al., 2013]. This matrix acts as protection against the effect of antibiotics, antiseptics and immunity system of organism. In the stage of mature biofilm, when the nutrients are depleted, the matrix of biofilm begins to fall apart under control in clusters, microorganisms detach and spread to new infection sites thus causing serious complications.

Treatment of topical infections, including chronic wounds and infections caused by biofilms adhering to artificial materials, is very difficult and the subsequences are alarming. Protection of our immunity against microorganisms in biofilms is not sufficient and impropriate applications of topical antibiotics or antiseptics may result to the occurrence of resistant strains of microorganisms which prevail over those sensitive. For an effective local therapy of infection caused by microbes in a biofilm, it is advisable to use combination of mechanical debridement with broad-spectrum antimicrobial agent and other compounds that penetrate inside the biofilm to kill bacteria or inhibit formation of biofilm. One of these possibilities is the application of commercially available wound dressings based on the local action of silver ions (Aquacel Ag+Extra). Action of powdered polymeric materials such Altrazeal is based on the providing ideal wound moisture which supports optimal cell function and regeneration of afflicted tissue.

One of the ways of increasing the therapeutic potential of local therapy of infected wound or preventing the infection adherence on the surface of artificial material is the application of antimicrobial peptides (AMP) [Zasloff, 2002]. It is well known that AMPs kill bacteria with mechanism of action which is markedly different from that of conventional antibiotics and does not develop bacterial resistance. Therefore AMPs are considered a promising supplement to, or substitute for, conventional antibiotics [Hancock and Sahl, 2006; Toke, 2005; Giuliani et al., 2007, Zaiou, 2007; Oyston et al., 2009; Baltzer and Brown, 2011; Yeung et al., 2011; Čeřovský, 2014].

Recently discovered and newly presented very effective AMPs represent convenient, synthetically available group of compounds aimed for the eradication of the infection or for the prevention of the emergence of the focus of infection. They can be applied in the combination with commercially available materials used as wound dressings, or as mixtures with carriers used in orthopedics for treatment of osteomyelitis, or as mixtures with synthetic polymeric materials used in orthopedics as the cements (polymethylmethacrylate) for endoprostheses fixation.

Antimicrobial peptides have been identified almost everywhere across the spectrum of animal and plant kingdoms. In the class of insects, AMPs represent a remarkable group which represent the main means of defense against microorganisms [Čeřovský, 2014; Otvos, 2000]. They kill bacteria and other microorganisms such as fungi with mechanism of action which is markedly different from that of conventional antibiotics and is assumed not to develop bacterial resistance. Although the precise mechanism of the broad spectrum of antimicrobial activity of these peptides is not yet fully understood, they appear to act via a specific, but not receptor-mediated, formation of trans-membrane pores or ion channels in cellular membrane. This causes leakage of essential metabolites that results in the disruption of microbial cell structure and leads to cell death [Oren and Shai, 1998; Yeaman and Yount, 2003; Nguyen at al., 2011]. Quite peculiar groups of peptides with antimicrobial properties were identified in the venom of stinging insects such as hymenopterans [Kuhn-Nentwig, 2003].

Antimicrobial effect of peptides isolated from the venoms of wasps, bees, bumblebees and ants is mostly secondary in the nature. Their main function consists of the toxicity, causing pain and inflammation, as it is in the case of peptides belonging to the group of mastoparans [Čeřovskýet al. 2008]. Nevertheless, antimicrobial effect of peptides isolated for example from the venom of wild bees is quite significant. With regard to their synthetic availability, these peptides may find application in practical medicine. The growing resistance of bacterial pathogens and yeasts to conventional antibiotics or commonly used antifungals has become serious global health problem which requires a persistent search for novel alternatives to traditional antibiotics. In such alarming situation, AMPs appear to be very promising compounds for developing drugs to fight resistant pathogens.

Natural peptide called hylanine was originally isolated from the venom reservoirs of solitary wild bees *Hylaeus signatus*, and its sequence was determined as follows:

(SEQ ID NO. 1)
H-Gly-Ile-Met-Ser-Ser-Leu-Met-Lys-Lys-Leu-Ala-Ala-His-Ile-Ala-Lys-NH$_2$

Based on this sequence, hylanine was prepared by the method of solid phase peptide synthesis followed by testing of its antimicrobial activity.

Synthetically prepared hylanine exhibited high antimicrobial activity against *Micrococcus luteus* and *Bacillus subtilis* and moderate activity against the yeast *Candida albicans*. However, its activity against all strains of pathogenic *Staphylococcus aureus* and *Pseudomonas aeruginosa* was weak. Nevertheless, its toxicity against eukaryotic cells measured as hemolytic activity was very low.

Even though the primary role of hylanine in the nature is not known, we deal with novel unique peptide with significant biological properties. However, it is generally known, that the peptides isolated from the venom of the insect of the Hymenoptera order exhibit antimicrobial and antifungal effect, eventually kill the cells of protozoal parasites or some cancer cells.

Disclosure of the Invention

It has surprisingly been found that a targeted replacement of several amino acids in the hylanine sequence resulted in hylanine analogs with strong antimicrobial effect against both pathogenic staphylococci and Gram-negative bacteria *Pseudomonas aeruginosa*, but also against the yeast *Candida albicans*. Some of these analogs exhibit also high efficacy against other pathogenic strains of *Candidas*.

Considerable antimicrobial effect of presented analogs was also shown in the course of their action on microbial biofilms in vitro formed by *C. albicans, P. aeruginosa* or *S. aureus*.

In these cases, the effect of the analogs was followed as the decrement of the metabolic activity of the microbial cells embedded inside the biofilms utilizing 2,3-bis-(2-methoxy-4-nitro-5-sulphophenyl)-2H-tetrazolium-5-carboxanilide (XTT) or 3-(4,5-dimethylthiazol-2-yl)-2,5-diphenyl-2H-tetrazolium bromide (MTT). The decrement of metabolic activity of microbial cells in the case of some analogs was comparable to those observed for commonly used antifungals or antibiotics or, in some cases, it was higher.

The present invention provides antimicrobial peptides of the general formula (I-A)
(SEQ ID NO. 2)
a-Ile-b-c-d-e-f-Lys-Lys-g-h-i-j-Ile-k-Lys-NH$_2$, where
a is Gly, Lys or β-Ala,
b is Met, Leu, Nle, Ile, Trp, Val or Phe,
c is Ser, Lys, Arg or Orn,
d is Ser, Lys, Arg or Orn,
e is Leu, Nle, Ile, Trp, Val or Phe,
f is Met, Leu, Nle, Ile, Trp, Val or Phe,
g is Leu, Nle, Ile or Trp,
h is Lys, Arg, Orn or Ala,
i is Lys, Arg, Orn or Ala,
j is Ile, Leu, Nle or His,
k is Lys, Arg, Orn or Ala,
whereas amino acid in any single position, or in several positions, or in all positions may be in D-configuration.

Subject matter of the invention involves also peptides of particular formulae from I to XIX (I)
(SEQ ID NO. 3)
H-Gly-Ile-Met-Ser-Ser-Leu-Met-Lys-Lys-Leu-Lys-Lys-Ile-Ile-Ala-Lys-NH$_2$, (II)
(SEQ ID NO. 4)
H-*Gly-Ile-Met-Ser-Ser-Leu-Met-Lys-Lys-Leu-Lys-Lys-Ile-Ile-Ala-Lys*-NH$_2$,, (III)
(SEQ ID NO. 5)
H-Gly-Ile-Leu-Ser-Ser-Leu-Leu-Lys-Lys-Leu-Lys-Lys-Ile-Ile-Ala-Lys-NH$_2$,, (IV)
(SEQ ID NO. 6)
H-*Gly-Ile-Leu-Ser-Ser-Leu-Leu-Lys-Lys-Leu-Lys-Lys-Ile-Ile-Ala-Lys*-NH$_2$,, (V)
(SEQ ID NO. 7)
H-Gly-Ile-Nle-Ser-Ser-Leu-Nle-Lys-Lys-Leu-Lys-Lys-Ile-Ile-Ala-Lys-NH$_2$,, (VI)
(SEQ ID NO. 8)
H-Lys-Ile-Leu-Ser-Ser-Leu-Leu-Lys-Lys-Leu-Lys-Lys-Ile-Ile-Ala-Lys-NH$_2$,, (VII)
(SEQ ID NO. 9)
H-Gly-Ile-Met-Ser-Ser-Leu-Met-Lys-Lys-Leu-Lys-Lys-Ile-Ile-Lys-Lys-NH$_2$,, (VIII)
(SEQ ID NO. 10)
H-Gly-Ile-Met-Ser-Ser-Leu-Met-Lys-Lys-Leu-Ala-Ala-His-Ile-Lys-Lys-NH$_2$,, (IX)
(SEQ ID NO. 11)
H-Gly-Ile-Met-Ser-Ser-Leu-Met-Lys-Lys-Leu-Ala-Ala-Ile-Ile-Lys-Lys-NH$_2$,, (X)
(SEQ ID NO. 12)
H-Gly-Ile-Leu-Lys-Ser-Leu-Leu-Lys-Lys-Leu-Lys-Lys-Ile-Ile-Ala-Lys-NH$_2$,, (XI)
(SEQ ID NO. 13)
H-Gly-Ile-Leu-Ser-Lys-Leu-Leu-Lys-Lys-Leu-Lys-Lys-Ile-Ile-Ala-Lys-NH$_2$,, (XII)
(SEQ ID NO. 14)
H-Gly-Ile-Leu-Ser-Ser-Leu-Trp-Lys-Lys-Leu-Lys-Lys-Ile-Ile-Ala-Lys-NH$_2$,, (XIII)
(SEQ ID NO. 15)
H-*Gly-Ile-Leu-Ser-Ser-Leu-Trp-Lys-Lys-Leu-Lys-Lys-Ile-Ile-Ala-Lys*-NH$_2$,, (XIV)
(SEQ ID NO. 16)
H-Gly-Ile-Trp-Ser-Ser-Leu-Leu-Lys-Lys-Leu-Lys-Lys-Ile-Ile-Ala-Lys-NH$_2$,, (XV)
(SEQ ID NO. 17)
H-Gly-Ile-Leu-Ser-Ser-Trp-Leu-Lys-Lys-Leu-Lys-Lys-Ile-Ile-Ala-Lys-NH$_2$,, (XVI)
(SEQ ID NO. 18)
H-Gly-Ile-Leu-Ser-Ser-Leu-Leu-Lys-Lys-Trp-Lys-Lys-Ile-Ile-Ala-Lys-NH$_2$,, (XVII)
(SEQ ID NO. 19)
H-Gly-Ile-Leu-Ser-Ser-Leu-Trp-Lys-Lys-Leu-Lys-Lys-Trp-Ile-Ala-Lys-NH$_2$,, (XVIII)
(SEQ ID NO. 20)
H-Gly-Ile-Leu-Ser-Ser-Leu-Leu-Lys-Lys-Leu-Lys-Lys-Trp-Ile-Ala-Lys-NH$_2$,, -continued (XIX)
(SEQ ID NO. 21)
H-Gly-Ile-Leu-Ser-Ser-Leu-Trp-Lys-Lys-Leu-Lys-Lys-
Ile-Ile-Ala-Lys-NH$_2$,, where amino acids in D-configuration are shown in italics.

Subject matter of the invention also involves peptides of the general formula I-A and peptides of formulae from I to XIX for use in the treatment or prevention of topical infections selected from a group which comprises chronic or difficult-to-heal wounds and skin disorders, mucosal infections and infectious bone and surrounding tissues diseases, including those which are caused by the formation of microbial biofilms.

Subject matter of the invention also involves peptides of the general formula I-A and peptides of formulae from I to XIX for use in prevention or elimination the infectious agent from catheters, joint and bone replacement and cement materials and for preventing intermediary for the infection of orthopedic implants.

Subject matter of the invention further involves peptides of the general formula I-A and peptides of formulae from I to XIX for use in the augmentation the effect of locally acting antibacterial medicaments and wound dressings used for the treatment of topical infections.

Subject matter of the invention also involves peptides of the general formula I-A and peptides of formulae from I to XIX for use in the incorporation into local carriers used in orthopedics, selected from the group comprising calcium phosphate, calcium sulphate, bioactive glass, apatite/wollastonite bioactive glass-ceramics, hydrogels, collagen, hone grafts, bone cement or synthetic polymers made from polymethylmethacrylate, copolymer of polymethylmethacrylate and hydroxypolymethylmethacrylate, polyanhydride, polylactide, polyglycolide, copolymers of hydroxybutyrate, hydroxyvalerate, polyhydroxyalkanoate, polycaprolactone or glycerol gelatin sponge, or composites made of polymers and inorganic carriers.

Subject matter of the invention also involves peptides of the general formula I-A and peptides of formulae from I to XIX for the production of the medicament for the treatment or prevention of topical infections chosen from a group, comprising difficult-to-heal wounds and skin disorders, mucosal infections and infectious diseases of bone and surrounding tissues.

Subject matter of the invention also involves a pharmaceutical composition which contains therapeutically effective amount of at least one peptide of the general formula I-A and/or peptide of the formula from I to XIX, optionally second active ingredient which can be antibiotic, antifungal agent and/or disinfection reagent, optionally also at least one pharmaceutically acceptable wound dressing, carrier, filling material and/or diluent.

Subject matter of the invention also involves a pharmaceutical composition for use in the treatment or prevention of topical infections chosen from a group comprising difficult-to-heal wounds and skin disorders, mucosal infections and infectious diseases of bone and surrounding tissues, for the prevention of infectious complications after implantation of joint replacements and after osteosynthesis, including those infections that are caused by the formation of microbial biofilms.

Subject matter of the invention also involves disinfection product which contains at least one peptide of the general formula I-A or peptide of the formula from I to XIX.

Presented invention thus involves peptides of the general formula I-A or peptides of particular formulae from I to XIX applicable for the treatment of chronic wounds infections, namely venous leg ulcers, diabetic foot syndrome and treatment of bone infection (osteomyelitis), where the local application of antimicrobial peptides also involves their incorporation into the local carriers used in orthopedics, hereafter for the prevention or eradication of infectious agent from joint replacements and cement fixations and for the prevention of postoperative infectious complications arising after implantation of joint replacements and osteosynthesis.

Furthermore, these peptides can be utilized for the treatment of the external ear canal infection (otitis externa), inflammation of eye conjunctiva (conjunctivitis acuta, conjunctivitis chronica), in gynecology as a formulation against vaginal infection caused by yeast, further at the treatment of burn wound infections or combat wound infections, namely in the cases when the commonly used disinfectant or antibiotics fail owing to antimicrobial resistance. Such infections are hardly curable as they are in the majority of cases complicated by the occurrence of biofilms in which the microorganisms may be thousand times more resistant to antimicrobial compounds compared to their planktonic cells.

Application of presented peptides added to sanitary and disinfection products seems to be also profitable.

Another aspect of the invention is also that the above mentioned pharmaceutical composition is designated for the treatment or prevention of the infections which are caused by the formation of microbial biofilms.

Synthetic peptides of the formulae from (I) to (XIX) may be included in the group of hylanines named according to the natural peptide hylanine. Proper replacement of amino acids in the hylanine sequence, for that exchange of more than one amino acid residues in proper combination had to be surprisingly made, resulted unexpectedly not only in the substantial enhancement of antimicrobial effect against pathogenic bacteria and yeasts, but also in the minimization of hemolytic activity. This approach made these presented peptides also suitable for the applications in the presence of eukaryotic cells. This facilitates their application as active components of human and veterinary medications. Sequences of analogs obtained by this approach and their molecular masses are shown in Table 1. Their antimicrobial activities against a series of bacteria expressed as MIC values (minimum inhibitory concentration) resulting from performed changes are shown in Table 2. Table 2 also shows values of antifungal activity against the yeast *Candida albicans* and the values of hemolytic activity.

Activities against a series of the yeasts of other strains of *Candida* are shown in Table 3.

Presented antimicrobial peptides may be used as components which enhance the efficacy of locally acting antimicrobial medicaments and wound dressings used for the treatment of topical infections. Their incorporation into the local carriers used in orthopedics is also proposed.

Another utilization of new antimicrobial peptides according to this invention includes, in addition to surface wounds and skin defects, treatment of bone infections (osteomyelitis), optionally a prevention or eradication of the infectious complications of endoprostheses and osteosyntheses and also their utilization in sanitary and disinfection products.

Antimicrobial effects of presented peptides were tested both against a series of microorganisms in planktonic form and against microbial biofilms. The effect of peptides against planktonic microorganisms is described hereafter in the examples 2 and 4; obtained results are summarized in Tables 2 and 3. Effects of the peptides against bacterial and yeast biofilms are described in examples 5 and 6, and the obtained results are summarized in Tables 4 and 5.

Selected peptides were also tested in the combination with antibiotics in order to verify their synergistic effect against *P. aeruginosa* and *S. aureus* in their planktonic forms. This is described in example 7 and summarized in Table 6.

Selected peptides were further tested in the models of induced osteomyelitis as described in example 8. Study of the antifungal action of peptides is described in example 9 and the result of these experiments is documented in FIGS. 1 A, B.

BRIEF DESCRIPTION OF THE DRAWINGS

FIG. 1 (B) represents the effect of fifteen minutes lasting action of ODDC, peptides II and VII alone, and in their combination on the survival of the yeast *C. glabrata* ATCC 2001.

EXAMPLES

Figure 1A:
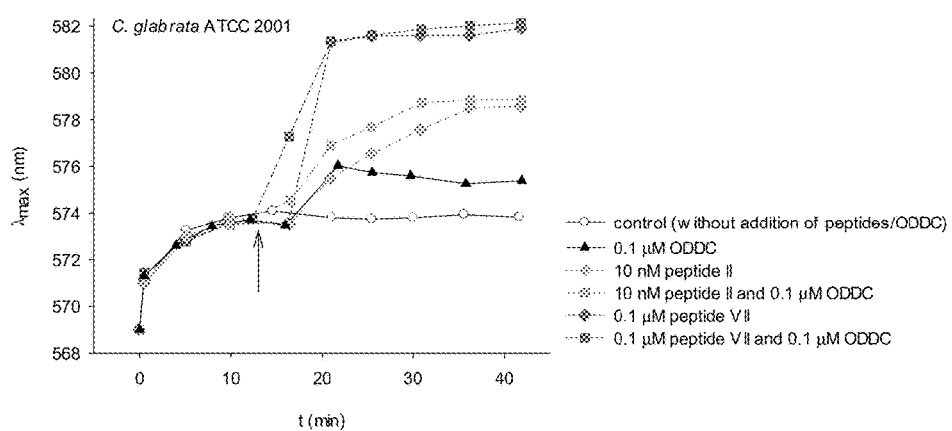
FIG. 1 (A) represents the effect of sub-inhibitory concentrations of octenidine dihydrochloride (ODDC), of peptides II and VII alone, and of the peptides in the combinations with ODDC on the yeast *C. glabrata* ATCC 2001, measured using a fluorescent probe diS-$C_3$(3). Arrow indicates the addition of the compounds to the cell suspensions.

List of Abbreviations
Fmoc 9-fluorenylmethyloxycarbonyl
MBHA resin 4-methylbenzhydrylamine resin
TFA trifluoroacetic acid
TIS triisopropylsilane
HPLC high performance liquid chromatography
BHI medium brain-heart infusion medium
YPD medium yeast extract peptone dextrose medium
LB medium Luria-Bertani medium
CFU colony forming units
ODDC octenidine dyhrochloride

Example 1

Synthesis of the Compounds of the Formulae I up to XIX

Antimicrobial peptides of the formulae from I to XIX were prepared manually in 5 ml polypropylene syringes with a polypropylene filter on the bottom using the methodology of solid phase peptide synthesis (SPPS). Syntheses were done according to $N^\alpha$-Fmoc chemistry protocol [Fields and Noble, 1990] on a Rink Amide MBHA resin (IRIS Biotech GmBH, Germany) (110 mg) with 0.7 mmol/g substitution. Protected amino acids were coupled in fourfold excess in dimethylformamide as solvent and N,N'-diisopropylcarbodiimide (7 equivalents)/1-hydroxybenzotriazole (5 equivalents) as coupling reagents. De-protection of the α-amino groups was performed with 20% piperidine in N,N-dimethylformamide. Crude peptides were de-protected and cleaved from the resin with a mixture of trifluoroacetic acid/1,2-ethanedithiol/water/thioanisol/triisopropylsilane (90:2.5:2.5:3:2) for 3.5 h and precipitated with tert-butyl methyl ether. The mixture of trifluoroacetic acid/water/triisopropylsilane (95:2.5:2.5) was used for the deprotection and cleavage of the peptides which did not contain methionine in their sequences. Usually, crude peptides were obtained in the amount of 100-120 mg. Part of this material (30 mg) of each peptide was in all cases purified by preparative RP-HPLC using a Vydac C-18 column (250×10 mm) at a flow rate 3.0 ml/min and using the gradient of solvents from 5% to 70% acetonitrile/water/0.1% TFA over 60 min yielding 10-15 mg of HPLC pure peptides. Their identities were verified by mass spectrometry as shown in Table 1.

TABLE 1

Amino acid sequences and molecular masses of the analogs of hylanine

| | | Molecular mass (Da) | |
|---|---|---|---|
| Peptide | sequence | Calculated | Found |
| I | Gly-Ile-Met-Ser-Ser-Leu-Met-Lys-Lys-Leu-Lys-Lys-Ile-Ile-Ala-Lys-NH$_2$ | 1787.13 | 1786.8 |
| II | Gly-*Ile-Met-Ser-Ser-Leu-Met-Lys-Lys-Leu-Lys-Lys-Ile-Ile-Ala-Lys*-NH$_2$ | 1787.13 | 1787.1 |
| III | Gly-Ile-Leu-Ser-Ser-Leu-Leu-Lys-Lys-Leu-Lys-Lys-Ile-Ile-Ala-Lys-NH$_2$ | 1751.21 | 1751.6 |
| IV | Gly-*Ile-Leu-Ser-Ser-Leu-Leu-Lys-Lys-Leu-Lys-Lys-Ile-Ile-Ala-Lys*-NH$_2$ | 1751.21 | 1751.2 |
| V | Gly-Ile-Nle-Ser-Ser-Leu-Nle-Lys-Lys-Leu-Lys-Lys-Ile-Ile-Ala-Lys-NH$_2$ | 1751.21 | 1751.6 |
| VI | Lys-Ile-Leu-Ser-Ser-Leu-Leu-Lys-Lys-Leu-Lys-Lys-Ile-Ile-Ala-Lys-NH$_2$ | 1822.29 | 1822.2 |
| VII | Gly-Ile-Met-Ser-Ser-Leu-Met-Lys-Lys-Leu-Lys-Lys-Ile-Ile-Lys-Lys-NH$_2$ | 1844.18 | 1843.9 |
| VIII | Gly-Ile-Met-Ser-Ser-Leu-Met-Lys-Lys-Leu-Ala-Ala-His-Ile-Lys-Lys-NH$_2$ | 1754.04 | 1754.0 |
| IX | Gly-Ile-Met-Ser-Ser-Leu-Met-Lys-Lys-Leu-Ala-Ala-Ile-Ile-Lys-Lys-NH$_2$ | 1787.13 | 1787.2 |
| X | Gly-Ile-Leu-Lys-Ser-Leu-Leu-Lys-Lys-Leu-Lys-Lys-Ile-Ile-Ala-Lys-NH$_2$ | 1792.28 | 1792.3 |
| XI | Gly-Ile-Leu-Ser-Lys-Leu-Leu-Lys-Lys-Leu-Lys-Lys-Ile-Ile-Ala-Lys-NH$_2$ | 1792.28 | 1792.3 |

TABLE 1-continued

Amino acid sequences and molecular masses of the analogs of hylanine

| Peptide | sequence | Molecular mass (Da) Calculated | Found |
|---|---|---|---|
| XII | Gly-Ile-Leu-Ser-Ser-Leu-Trp-Lys-Lys-Leu-Lys-Lys-Ile-Ile-Ala-Lys-NH$_2$ | 1824.21 | 1824.2 |
| XIII | Gly-*Ile-Leu-Ser-Ser-Leu-Trp-Lys-Lys-Leu-Lys-Lys-Ile-Ile-Ala-Lys*-NH$_2$ | 1824.21 | 1824.2 |
| XIV | Gly-Ile-Trp-Ser-Ser-Leu-Leu-Lys-Lys-Leu-Lys-Lys-Ile-Ile-Ala-Lys-NH$_2$ | 1824.21 | 1824.2 |
| XV | Gly-Ile-Leu-Ser-Ser-Trp-Leu-Lys-Lys-Leu-Lys-Lys-Ile-Ile-Ala-Lys-NH$_2$ | 1824.21 | 1824.2 |
| XVI | Gly-Ile-Leu-Ser-Ser-Leu-Leu-Lys-Lys-Trp-Lys-Lys-Ile-Ile-Ala-Lys-NH$_2$ | 1824.21 | 1824.2 |
| XVII | Gly-Ile-Leu-Ser-Ser-Leu-Trp-Lys-Lys-Leu-Lys-Lys-Trp-Ile-Ala-Lys-NH$_2$ | 1897.20 | 1897.2 |
| XVIII | Gly-Ile-Leu-Ser-Ser-Leu-Leu-Lys-Lys-Leu-Lys-Lys-Trp-Ile-Ala-Lys-NH$_2$ | 1824.21 | 1824.2 |
| XIX | Gly-Ile-Leu-Ser-Ser-Leu-Trp-Lys-Lys-Leu-Lys-Lys-Ile-Ile-Ala-Lys-NH$_2$ | 1824.21 | 1824.2 |

Example 2

Determination of an Antimicrobial Activity

Gram-positive bacteria (*Micrococcus luteus, Bacillus subtilis, Staphylococcus aureus, Staphylococcus epidermidis* and *Enterococcus faecalis*), Gram-negative bacteria (*Escherichia coli* and *Pseudomonas aeruginosa*) and the yeast (*Candida albicans*) were grown to exponential phase and then were diluted with fresh medium. BHI medium (Oxoid, Great Britain) was used for *Enterococcus faecalis*; YPD medium containing yeast extract peptone and glucose was used for *Candida albicans* and LB medium (Sigma, Czech Republic) was used for the remaining microorganisms. Then the microorganisms were added to the solutions of the tested antimicrobial peptides in LB medium in multi-well plates. The final peptide concentration it the wells was in the range of 0.1 to 100 $\mu mol.l^{-1}$. That was made by twofold serial dilution from the peptide stock solution (1 $mmol.l^{-1}$). The plates were incubated at 37° C. for 20 h while being continuously shaken in a Bioscreen C (Oy Growth Curves AB Ltd., Helsinki, Finland). Absorbance was measured at 540 nm every 15 min. Antimicrobial activity (Table 2) was determined as a quantitative minimum inhibitory concentration (MIC) by observing bacterial growth in the presence of different concentrations of tested peptides. In the experiments ca $10^5$ CFU of bacteria or candida per well were routinely used. Tetracycline in a concentration range of 0.1-100 $\mu mol.l^{-1}$ was used as a standard.

Multiresistant clinical isolates of bacteria were obtained from University Hospital in Motol, Prague, Czech Republic and from Liberec Regional Hospital, Czech Republic. Methicillin resistant *Staphylococcus aureus* (MRSA) 6271 and *Pseudomonas aeruginosa* 5482 were from the Czech National Collection of Type Cultures, the National Institute of Public Health, Prague, Czech Republic. Other bacteria were from the Czech Collection of Microorganisms, Brno, Czech Republic. Candida albicans came from the Faculty of Medicine, Palacky University, Olomouc, Czech Republic.

Example 3

Determination of a Hemolytic Activity

The peptides in the concentrations 2-200 $\mu mol.l^{-1}$ were incubated with the suspension of human red blood cells (5% v/v) for 1 h at 37° C. in a physiological solution at a final volume of 0.2 ml. The samples were then centrifuged for 5 min at 250 g, and the absorbance of the supernatant was determined at 540 nm. Supernatants of red blood cells suspended in physiological solution and in 0.2% (v/v) TRITON X100 in physiological solution served as controls for zero hemolysis (blank) and 100% hemolysis, respectively. Hemolytic activity is expressed as the peptide concentration required for lysis of 50% of human erythrocytes in the assay ($LC_{50}$). The results of tests are shown in Table 2.

TABLE 2

Antimicrobial and hemolytic activity of (I) up to (XIX) peptides and tetracycline.

| Peptid | Antimicrobial activity MIC ($\mu mol \cdot l^{-1}$) | | | | | | | | | | | Hemolytic activity $LC_{50}$ ($\mu mol \cdot l^{-1}$) |
|---|---|---|---|---|---|---|---|---|---|---|---|---|
| | M. l. | B. s. | S. a. Liberec | S. a. 6271 | S. a. Motol | S. e. Motol | E. f. Motol | E. c. | P. a. Liberec | P. a. 5482 | C. a. Olomouc | |
| I | 1.9 | 5.7 | 7.6 | 32.0 | 23.0 | 1.9 | 100.0 | 9.0 | 7.4 | 5.0 | 5.2 | >400 |
| II | 1.3 | 2.2 | 7.5 | 12.7 | 16.2 | 2.2 | 44.3 | 6.3 | 8.5 | 3.2 | 8.0 | >400 |
| III | 1.6 | 2.0 | 3.8 | 16.0 | 5.0 | 1.8 | 59.3 | 8.0 | 7.5 | 5.0 | 10.0 | 284.2 |
| IV | 1.8 | 1.8 | 2.6 | 5.7 | 6.3 | 3.2 | 6.7 | 4.5 | 9.7 | 4.5 | 9.0 | 332.9 |

TABLE 2-continued

Antimicrobial and hemolytic activity of (I) up to (XIX) peptides and tetracycline.

| Peptid | M. l. | B. s. | S. a. Liberec | S. a. 6271 | S. a. Motol | S. e. Motol | E. f. Motol | E. c. | P. a. Liberec | P. a. 5482 | C. a. Olomouc | Hemolytic activity $LC_{50}$ ($\mu mol \cdot l^{-1}$) |
|---|---|---|---|---|---|---|---|---|---|---|---|---|
| V | 1.6 | 3.5 | 4.0 | 12.7 | 6.7 | 2.5 | 54.0 | 10.0 | 7.9 | 4.0 | 10.0 | 373.4 |
| VI | 1.0 | 1.3 | 5.5 | 32.0 | 10.0 | 1.4 | 32.5 | 16.0 | 16.0 | 5.0 | 25.3 | 363.7 |
| VII | 1.9 | 2.5 | 18.0 | 54.0 | 64.7 | 1.7 | >100 | 22.0 | 9.9 | 7.1 | 6.3 | >400 |
| VIII | 1.6 | 2.8 | 76.7 | 85.3 | 90.0 | 11.3 | >100 | 20.0 | 46.0 | 23.0 | 5.0 | >400 |
| IX | 1.3 | 2.5 | 8.8 | 35.0 | 18.3 | 3.1 | 98.0 | 16.0 | 10.6 | 5.4 | 8.0 | >400 |
| X | 1.4 | 1.5 | 4.3 | 16.5 | 10.0 | 2.2 | 76.7 | 10.0 | 8.9 | 5.0 | 24.0 | >400 |
| XI | 1.6 | 1.4 | 5.9 | 22.7 | 10.0 | 1.8 | 72.7 | 17.5 | 8.5 | 4.5 | 45.3 | >400 |
| XII | 0.8 | 1.1 | 2.1 | 5.3 | 5.0 | 2.0 | 25.3 | 3.4 | 8.8 | 5.3 | 10.7 | 196.6 |
| XIII | 1.6 | 1.6 | 3.1 | 6.3 | 3.2 | 1.7 | 3.4 | 5.0 | 8.8 | 6.7 | 8.0 | 190.7 |
| XIV | 0.8 | 0.8 | 4.6 | 20.0 | 5.3 | 1.5 | 46.0 | 1.6 | 21.0 | 6.3 | 16.0 | 165.4 |
| XV | 1.6 | 1.6 | 6.6 | 16.0 | 16.2 | 2.0 | 73.3 | 11.0 | 5.9 | 4.0 | 16.7 | >400 |
| XVI | 2.0 | 1.6 | 8.8 | 20.0 | 20.3 | 2.7 | 100.0 | 7.5 | 7.1 | 5.0 | 10.5 | >400 |
| XVII | n.t. | 1.3 | 1.6 | 2.5 | 2.0 | 1.6 | 10.0 | 2.5 | 24.1 | 12.7 | 12.7 | 57.2 |
| XVIII | n.t. | 1.3 | 2.5 | 8.0 | 4.0 | 1.6 | 25.3 | 4.0 | 20.7 | 8.0 | 16.0 | 159.6 |
| XIX | n.t. | 2.0 | 3.2 | 6.3 | 3.2 | 1.6 | 6.5 | 13.0 | 8.5 | 6.3 | 26.0 | >200 |
| Tetracyklin | 0.8 | 16.0 | 1.1 | 0.9 | 2.0 | >100 | 40.0 | 2.7 | 70.4 | 28.7 | n.t. | >200 |

M. l., *Micrococcus luteus*;
B. s., *Bacillus subtilis*;
S. a., *Staphylococcus aureus*;
S. e., *Staphylococcus epidermidis*;
E. f., *Enterococcus faecalis*;
E. c., *Escherichia coli*;
P. a., *Pseudomonas aeruginosa*;
C. a., *Candida albicans*;
n.t. = not tested Example 4

Determination of an Antifungal Activity Against Selected Series of Yeasts

All yeasts *Candida albicans* (Olomouc) and ATCC MYA-2876, *Candida glabrata* ATCC 2001 and DSY 565, *Candida dubliniensis* ATCC MYA-646, *Candida krusei* ATCC 6258 and *Candida tropicalis* ATCC 750 were sub-cultured from sterile vials onto Sabouraud dextrose agar, which was composed of 40 g dextrose (Penta, Czech Republic), 10 g peptone (OXOID, Great Britain) and 17 g agar (OXOID), dissolved in 1 l of distilled water, and cultivated for 24 hours at 35° C.

All strains were stored in a way that minimizes the possibility of mutation. *Candida* spp. were grown overnight in liquid YPD medium which is composed of 10 g yeast extract (DIFCO, USA), 20 g peptone (OXOID), and 20 g dextrose (Penta) dissolved in 1 l distilled water. Then the overnight culture was cryogenically preserved by suspending in 50% glycerol solution (1:1) in small vials and stored at −80° C.

The inoculum was prepared by picking five colonies from 24-hour-old cultures of *Candida* spp. The colonies were suspended in 1 ml of sterile saline solution and vortexed for 15 seconds. Optical density of the suspension was adjusted spectrophotometrically by adding sterile saline solution to produce optical density of 0.18 at 600 nm. A working suspension was made by a 1:50 dilution followed by a 1:20 dilution of the stock suspension with RPMI 1640 broth medium which was composed of L-glutamine without $NaHCO_3$ (BioSera, France), and with 0.165 $mol.l^{-1}$ MOPS (Duchefa, Netherland)—further as RPMI broth medium.

The broth microdilution test was performed by using sterile, disposable, multi-well microdilution plates (96-well). The peptides in the concentrations 0.625-160 $\mu mol.l^{-1}$ were pipetted into the wells in 100 µl volumes. Each well of the plate was inoculated with 100 µl of the diluted inoculum suspension. Final yeast density in each well was $5 \times 10^2$ up to $2.5 \times 10^3$ CFU/ml. The microdilution plates were incubated without shaking at 35° C. and observed for the presence or absence of visible growth for 48 hours.

Drug-free medium without inoculation served as negative control; the growth positive control contained inoculated drug-free medium. Amphotericin B was used as control drug to ensure quality of *Candida* strains.

The minimal inhibition concentrations (MICs) were visually determined 48 hours after inoculation. The MIC values were defined as the lowest concentration in which no observable growth is noticeable.

All yeast isolates were obtained from the Institute of Physiology of the Academy of Sciences of the Czech Republic. *Candida albicans* (Olomouc) came from the Faculty of Medicine and Dentistry, Palacý University Olomouc.

TABLE 3

Antifungal activity of (I) up to (XVIII) peptides and antifungal compounds

| Peptide | C. albicans Olomouc | C. albicans ATCC MYA-2876 | C. krusei ATCC 6258 | C. tropicalis ATCC 750 | C. dubliniensis ATCC MYA-646 | C. glabrata ATCC 2001 | C. glabrata DSY 565 |
|---|---|---|---|---|---|---|---|
| I | 17.0 | 22.0 | 10.0 | 0.8 | 40.0 | 40.0 | 88.9 |
| II | 15.5 | 15.5 | 7.8 | 0.7 | 34.0 | 15.5 | 32.2 |
| III | 13.0 | 18.0 | 5.0 | 0.9 | 20.0 | 24.0 | 44.0 |

Antifungal activity MIC ($\mu mol \cdot l^{-1}$)

TABLE 3-continued

Antifungal activity of (I) up to (XVIII) peptides and antifungal compounds

| | Antifungal activity MIC ($\mu mol \cdot l^{-1}$) | | | | | | |
|---|---|---|---|---|---|---|---|
| Peptide | C. albicans Olomouc | C. albicans ATCC MYA-2876 | C. krusei ATCC 6258 | C. tropicalis ATCC 750 | C. dubliniensis ATCC MYA-646 | C. glabrata ATCC 2001 | C. glabrata DSY 565 |
| IV | 11.0 | 11.0 | 4.3 | 0.6 | 12.0 | 10.0 | 20.0 |
| V | 12.0 | 19.0 | 5.0 | 1.0 | 26.0 | 24.0 | 44.0 |
| VI | 12.0 | 20.0 | 4.8 | 0.9 | 12.0 | 28.0 | 71.1 |
| VII | 17.0 | 22.0 | 10.0 | 1.1 | 20.0 | 40.0 | 97.8 |
| VIII | 17.0 | 20.0 | 10.0 | 1.1 | 36.0 | 26.0 | 66.7 |
| IX | 16.0 | 18.0 | 12.0 | 1.1 | 42.0 | 20.0 | 44.4 |
| X | 10.5 | 17.0 | 5.0 | 1.0 | 14.0 | 34.0 | 71.1 |
| XI | 12.0 | 20.0 | 5.0 | 1.0 | 10.5 | 26.0 | 40.0 |
| XII | 8.5 | 10.0 | 4.3 | 1.0 | 9.5 | 10.0 | 21.0 |
| XIII | 10.0 | 11.0 | 5.0 | 1.1 | 9.5 | 6.0 | 18.0 |
| XIV | 8.2 | 10.0 | 5.2 | 1.2 | 9.0 | 19.1 | 48.0 |
| XV | 21.0 | 17.0 | 8.0 | 1.2 | 22.0 | 40.0 | 88.9 |
| XVI | 18.0 | 26.0 | 10.0 | 1.0 | 40.0 | 40.0 | 231.1 |
| XVII | 4.5 | 5.5 | 3.3 | 0.8 | 5.0 | 5.5 | 11.0 |
| XVIII | 8.5 | 10.0 | 7.8 | 1.2 | 10.0 | 8.5 | 24.0 |
| Fluconazole | 2.0 | 2.2 | 515.6 | 49.3 | 1.8 | 266.7 | 950 |
| Clotrimazole | 0.4 | 0.3 | 1.0 | 4.6 | 1.4 | 14.2 | 35.0 |

Example 5

Determination of an Antimicrobial Activity on the Models of Bacterial Biofilms

Inoculum of S. aureus (Liberec) or P. aeruginosa (Liberec) cultivated overnight in BHI medium was diluted with fresh BHI medium containing 1% glucose to a final concentration to be ca. $10^8$ CFU/ml. Then this was pipetted (100 µl) to 96-multiwell polystyrene plate which was incubated at 37° C. under rotary shaking (300 RPM) for 24 h. Medium without bacteria in the wells was used as a negative control. Supernatant from each well was drained and the biofilm formed on the bottom and on the walls of the wells was cautiously washed three times by sterile physiological solution (300 µl). The peptides tested in the concentrations of 1-128 $\mu mol.l^{-1}$ were prepared by twofold serial dilution of their stock solution (1 $mmol.l^{-1}$) in fresh BHI medium and then pipetted (100 µl) to the wells with formed biofilms. The biofilms covered by BHI medium without peptide were used as a positive control. The plates were then incubated for 20 h as described above. After that the liquid was drained out and wells were washed twice with sterile physiological solution.

The metabolic activity of surviving bacterial cells in the biofilm was determined by staining with MTT (3-(4,5-dimethylthiazol-2-yl)-2,5-diphenyl-2H-tetrazolium bromide) as follows: The mixture of BHI medium (100 µl) and 10 µl of the stock solution of MTT (5 mg/ml in physiological solution) was added to each well and the plate was incubated 40 min at 37° C. The liquid was drained out and the insoluble formazan crystals formed by reduction inside the biofilm were dissolved with dimethyl sulphoxide (100 µl). The intensity of staining in each well was measured as absorbance at 540 nm on a Tecan Infinite M200 Pro reader (Tecan GmbH, Austria). Remaining activity of surviving cells inside the biofilm was expressed for each well in percentage according to the following equation:

$$\% = \frac{A - A_{BL}}{A_C - A_{BL}} * 100,$$

where A is the absorbance of the tested compound, $A_{BL}$ is the absorbance of the negative control, and $A_C$ is the absorbance of control biofilm. The values of remaining metabolic activity are shown in Table 4.

TABLE 4

Effect of selected peptides on the bacterial biofilms formed by Staphylococcus aureus and Pseudomonas aeruginosa expressed as remaining metabolic activity of microbial cells (in percentages) at given peptide concentration (n.t., not tested)

| | Metabolic activity (%) S. aureus (Liberec) Peptide concentration | | | | | Metabolic activity (%) P. aeruginosa (Liberec) Peptide concentration | | | | |
|---|---|---|---|---|---|---|---|---|---|---|
| Peptide | 8 $\mu mol \cdot l^{-1}$ | 16 $\mu mol \cdot l^{-1}$ | 32 $\mu mol \cdot l^{-1}$ | 64 $\mu mol \cdot l^{-1}$ | 128 $\mu mol \cdot l^{-1}$ | 8 $\mu mol \cdot l^{-1}$ | 16 $\mu mol \cdot l^{-1}$ | 32 $\mu mol \cdot l^{-1}$ | 64 $\mu mol \cdot l^{-1}$ | 128 $\mu mol \cdot l^{-1}$ |
| I | 111.6 | 103.3 | 111.2 | 101.9 | 11.4 | 86.4 | 87.7 | 89.6 | 62.9 | 43.4 |
| II | 143.1 | 138.8 | 107.5 | 29.9 | 7.7 | 94.2 | 100.5 | 79.1 | 33.0 | 26.7 |
| III | 87.8 | 89.6 | 78.4 | 15.9 | 2.4 | n.t. | n.t. | n.t. | n.t. | n.t. |
| IV | 65.5 | 34.2 | 7.1 | 3.0 | 0.0 | 56.5 | 69.5 | 56.0 | 59.6 | 21.7 |
| V | 83.0 | 71.0 | 49.5 | 26.0 | 0.0 | 65.5 | 59.8 | 64.9 | 61.4 | 49.3 |
| VI | 55.6 | 34.0 | 15.1 | 4.4 | 0.1 | 79.0 | 74.1 | 75.7 | 89.2 | 56.8 |
| VII | n.t. | n.t. | n.t. | n.t. | n.t. | 77.3 | 76.5 | 71.3 | 53.3 | 33.8 |
| IX | 79.1 | 53.6 | 54.0 | 30.5 | 23.6 | 73.6 | 76.8 | 85.3 | 83.8 | 34.2 |
| X | 66.7 | 59.1 | 30.0 | 22.3 | 2.3 | 78.9 | 67.3 | 67.8 | 93.9 | 45.9 |
| XI | 75.2 | 68.4 | 51.0 | 24.0 | 0.0 | 79.4 | 60.9 | 82.9 | 83.1 | 49.1 |
| XII | 52.2 | 31.5 | 18.9 | 14.7 | 1.0 | 77.3 | 69.3 | 66.9 | 44.4 | 57.9 |

TABLE 4-continued

Effect of selected peptides on the bacterial biofilms formed by *Staphylococcus aureus* and *Pseudomonas aeruginosa* expressed as remaining metabolic activity of microbial cells (in percentages) at given peptide concentration (n.t., not tested)

| | Metabolic activity (%) *S. aureus* (Liberec) Peptide concentration | | | | | Metabolic activity (%) *P. aeruginosa* (Liberec) Peptide concentration | | | | |
|---|---|---|---|---|---|---|---|---|---|---|
| Peptide | 8 µmol · l$^{-1}$ | 16 µmol · l$^{-1}$ | 32 µmol · l$^{-1}$ | 64 µmol · l$^{-1}$ | 128 µmol · l$^{-1}$ | 8 µmol · l$^{-1}$ | 16 µmol · l$^{-1}$ | 32 µmol · l$^{-1}$ | 64 µmol · l$^{-1}$ | 128 µmol · l$^{-1}$ |
| XIII | 71.6 | 33.8 | 21.5 | 20.4 | 5.3 | 71.2 | 65.8 | 61.2 | 73.6 | 23.0 |
| XIV | 55.1 | 52.2 | 16.3 | 14.5 | 4.4 | 67.2 | 54.9 | 54.8 | 65.6 | 31.1 |
| XV | 71.5 | 60.5 | 40.6 | 38.0 | 6.9 | 64.1 | 70.3 | 57.6 | 63.2 | 32.2 |
| XVI | 58.0 | 60.6 | 64.6 | 18.4 | 8.7 | 74.1 | 66.2 | 57.6 | 47.5 | 31.9 |
| XVII | 72.1 | 12.3 | 2.6 | 5.4 | 7.7 | n.t. | n.t. | n.t. | n.t. | n.t. |
| XVIII | 68.7 | 46.7 | 19.5 | 10.5 | 3.6 | n.t. | n.t. | n.t. | n.t. | n.t. |
| XIX | 72.8 | 2.8 | 2.3 | 2.3 | 1.7 | n.t. | n.t. | n.t. | n.t. | n.t. |
| Vancomycin | 52.8 | 15.9 | 9.7 | 8.5 | 6.3 | n.t. | n.t. | n.t. | n.t. | n.t. |
| Amikacin | 95.4 | 102.4 | 108.7 | 82.4 | 104.0 | 80.0 | 62.9 | 40.4 | 20.3 | 11.8 |

Example 6

Determination of an Antimicrobial Activity on the Models of *C. albicans* Biofilms

*Candida albicans* (Olomouc) was sub-cultured overnight in YPD medium (10 g yeast extract (DIFCO, USA), 20 g peptone (OXOID), 20 g glucose (Penta) dissolved in 1 L of distilled water) at constant shaking (100 RPM) at 37° C. Next day, the overnight culture was diluted 1:100 into fresh YPD medium and incubated at constant shaking (200 RPM) at 37° C. until the mid-exponential growth phase was reached. Then the cells were harvested and washed twice by centrifugation in physiological solution (5000 RPM; 5 min). Cells were suspended in sterile salt solution and their optical density was determined at 600 nm.

A final yeast suspension was prepared at a cell density of 1×10$^6$ CFU (corresponding to optical density of 0.17 at 600 nm) in RPMI 1640 medium with L-glutamine (BioSera), NaHCO$_3$ (2 g/l; Penta) and 0.165 mol.l$^{-1}$ MOPS (Duchefa)—further as RPMI broth medium 1.

Biofilms were formed on commercially available sterile, polystyrene, flat-bottomed, 96-well microtiter plates (TPP, SW). Cell suspension (100 µl) was pipetted into selected wells of a microtiter plate and incubated without shaking for 2 hours at 37° C. Afterwards, the wells were washed twice with sterile PBS buffer (1.44 g Na$_2$HPO$_4$, 0.24 g KH$_2$PO$_4$, 0.2 g KCl and 8 g NaCl in 1 l distilled water, pH=7; Penta). Fresh RPMI broth medium 1 (100 µl) was added to each well and the plate was sealed with parafilm and incubated without shaking for 48 hours at 37° C.

Planktonic and non-adherent cells were removed by three-fold washing of the biofilm with sterile PBS buffer (200 µl). A twofold serial dilution was used to reach required peptide concentration (in RPMI broth medium 1) in each well. Peptide concentrations range was between 0.39-200 µmol.l$^{-1}$. Plates were then sealed with parafilm and incubated for 20 hours at 37° C.

The metabolic activity of surviving *Candida* cells in the treated biofilm was determined by staining with XTT (2,3-Bis(2-methoxy-4-nitro-5-sulphophenyl)-2H-tetrazolium-5-carboxanilide). Stock solution of PMS (phenazine methosulfate; 7.5 g/l; SIGMA, Czech Republic) stored at −20° C. was diluted in PBS buffer 1:100. Diluted PMS was further mixed (2:25) with stock solution of XTT (0.5 g/l; Alchimica, Slovakia) dissolved in PBS/RPMI broth medium (1:1). Mixture (100 µl) of PMS and XTT was added into treated biofilm in the wells and incubated for 90 min at 37° C. Then the intensity of staining in each well was measured as absorbance at 540 nm on a Tecan Infinite M200 Pro reader (Tecan GmbH, Austria). Remaining metabolic activity of the cells in the biofilm was expressed for each well in percentage and calculated as follows:

$$\% = \frac{A - A_{BL}}{A_C - A_{BL}} * 100,$$

where A is the absorbance of tested compound, $A_{BL}$ is the absorbance of negative control and $A_C$ is the absorbance of control untreated biofilm. The non-inoculated wells served as negative control. Inoculated wells not treated with compound served as positive control. Amphotericin B was used as control drug to ensure quality of *Candida albicans*. The values of remaining metabolic activity of treated biofilms are shown at Table 5.

TABLE 5

Effect of selected peptides on the microbial biofilms formed by *Candida albicans* (Olomouc) expressed as remaining metabolic activity of microbial cells (in percentages) at given peptide concentration.

| | Metabolic activity of *C. albicans* (%) Peptide concentration | | | | | |
|---|---|---|---|---|---|---|
| Peptide | 6.25 µmol · l$^{-1}$ | 12.5 µmol · l$^{-1}$ | 25 µmol · l$^{-1}$ | 50 µmol · l$^{-1}$ | 100 µmol · l$^{-1}$ | 200 µmol · l$^{-1}$ |
| I | 100.4 | 108.0 | 130.7 | 57.5 | 28.2 | 8.1 |
| II | 105.3 | 114.2 | 35.2 | 1.0 | 0.0 | 0.0 |
| III | 104.7 | 113.6 | 87.2 | 31.1 | 28.4 | 0.0 |
| IV | 106.9 | 37.2 | 6.0 | 2.3 | 2.1 | 0.5 |
| V | 106.4 | 89.5 | 45.0 | 6.9 | 2.4 | 0.4 |

TABLE 5-continued

Effect of selected peptides on the microbial biofilms formed by *Candida albicans* (Olomouc) expressed as remaining metabolic activity of microbial cells (in percentages) at given peptide concentration.

| Peptide | Metabolic activity of *C. albicans* (%) Peptide concentration | | | | | |
|---|---|---|---|---|---|---|
| | 6.25 µmol · l$^{-1}$ | 12.5 µmol · l$^{-1}$ | 25 µmol · l$^{-1}$ | 50 µmol · l$^{-1}$ | 100 µmol · l$^{-1}$ | 200 µmol · l$^{-1}$ |
| VI | 98.8 | 111.2 | 110.5 | 28.3 | 0.4 | 0.0 |
| VII | 104.6 | 116.0 | 120.7 | 31.5 | 22.0 | 0.0 |
| VIII | 99.4 | 99.1 | 105.6 | 112.2 | 106.8 | 53.0 |
| IX | 93.2 | 54.3 | 2.3 | 1.5 | 1.3 | 0.8 |
| X | 100.8 | 109.3 | 65.3 | 16.8 | 7.0 | 3.3 |
| XI | 97.7 | 70.3 | 79.3 | 32.8 | 7.6 | 6.1 |
| XII | 86.8 | 80.3 | 94.8 | 63.6 | 6.2 | 3.2 |
| XIII | 78.3 | 56.9 | 37.2 | 10.9 | 5.8 | 4.9 |
| XIV | 84.6 | 80.9 | 91.1 | 14.2 | 7.4 | 4.2 |
| XV | 94.9 | 92.8 | 73.8 | 65.2 | 9.4 | 3.4 |
| XVI | 97.3 | 103.2 | 68.5 | 68.1 | 44.9 | 11.4 |
| XVII | 2.4 | 1.0 | 0.9 | 1.3 | 2.3 | 1.5 |
| XVIII | 11.5 | 2.5 | 3.2 | 3.2 | 3.1 | 2.6 |
| Fluconazole | 33.5 | 30.8 | 31.7 | 30.7 | 32.4 | 29.2 |
| Clotrimazole | 39.7 | 37.6 | 34.2 | 28.4 | 21.8 | 22.2 |

Example 7

Synergistic Effect Between Peptides and Commonly Used Antibiotics Against *S. aureus* and *P. aeruginosa*

MICs values of various combinations of two fold serial dilutions of peptides and antibiotics were determined using the same methodology as in the case of antimicrobial activity determination (Example 2). To consider the type of the final effect, FIC indexes (fractional inhibitory concentration) were used and calculated as follows:

$$FIC = \frac{MIC_{PC}}{MIC_P} + \frac{MIC_{AC}}{MIC_A},$$

where $MIC_{PC}$ and $MIC_{AC}$ are the MICs of the peptide and antibiotic in combination, respectively, and $MIC_P$ and $MIC_A$ are the MICs of the peptide and antibiotic tested alone, respectively. FIC<0.5 were considered as synergy, 0.5≤FIC≤2 as addition effect, and FIC>2 as antagonism. Table 6 shows examples of the synergistic effect of the combination of selected peptides with tetracycline (TET) and with rifampicin (RIF) against *P. aeruginosa* (Liberec) and with the amoxicillin (AMX) against *S. aureus* (Liberec).

TABLE 6

FIC indexes for the combination of selected peptides with antibiotics against *S. aureus* (Liberec) and *P. aeruginosa* (Liberec).

| Peptide | FIC indexes (fractional inhibitory concentration) | | |
|---|---|---|---|
| | Combination with TET against *P. aeruginosa* | Combination with RIF against *P. aeruginosa* | Combination with AMX against *S. aureus* |
| I | 0.646 | 0.427 | 0.333 |
| II | 0.667 | 0.323 | n.t. |
| III | 0.542 | 0.385 | 0.688 |
| IV | 0.750 | 0.302 | n.t. |
| VI | 0.708 | 0.260 | 0.292 |
| VII | 0.625 | 0.365 | 0.167 |
| IX | 0.542 | 0.417 | n.t. |
| X | 0.521 | 0.333 | 0.542 |
| XI | 0.646 | 0.344 | 0.333 |
| XII | 0.646 | 0.438 | n.t. |
| XIII | 0.583 | 0.292 | n.t. |
| XIV | 0.354 | 0.271 | 0.396 |
| XV | 0.646 | 0.396 | 0.375 |
| XVI | 0.583 | 0.417 | n.t. |
| XVII | 0.417 | 0.292 | n.t. |
| XVIII | 0.625 | 0.271 | n.t. | n.t.—not tested;
FIC <0.5 = synergism, 0.5 ≤ FIC ≤ 2 = additive effect, FIC >2 = antagonism. The values shown are averages of three independent experiments.

Example 8

Peptides XII and XIII Acting in the Focus of Infection in the Model of Induced Osteomyelitis Three bored holes of the size ca. 5 mm in diameter and 10 mm in deep were drilled by surgical spoon in the place of the resection into the spongy part of two defrosted heads of human hip joints. These two graft bones were then placed into beakers, and they were cushioned with sterile gauze which was moisturized with physiological solution to prevent bone drying. The suspension of *Staphylococcus aureus* (Motol) in LB medium (50-100 µl) in the concentration 10$^9$ was pipetted into all holes in one bone graft and the suspension of *Staphylococcus epidermidis* in the same concentration was pipetted into the holes of the second bone. The beakers were covered by Petri dish and kept at room temperature in dark for 24 h.

After that one of these holes was wiped out with sterile wet swab. The swab was extracted with physiological solution (400 µl), the extract was tenfold serially diluted and plated onto LB agar in Petri dishes and incubated for one day in order to evaluate the bacterial growth. The second hole was filled with the local carrier blended with a mixture of the peptides nos. XII and XIII. For the comparison, the remaining third hole was filled with the carrier alone. The carrier named ChronOS Inject was used as two components product supplied by the company Synthes GmbH, Switzerland. The powder component contains calcium phosphate blended with additives and the liquid component is 0.5% hyaluronic acid. The paste for filling the holes was prepared by successive mixing the powder component (200 mg) with the peptides nos. XII (8 mg) and XIII (4 mg) and the liquid component (70 μl). The paste without peptides used for comparison was prepared by the same manner.

After two days, the fillings were thoroughly removed with surgical spoon and the empty holes were expansively wiped out by wet swabs, the swabs were extracted with physiological solution (400 μl), and the extracts were plated on the agar in Petri dishes in tenfold serial dilution. Following an overnight incubation, the number of bacterial colonies was counted.

The experiments were evaluated by the comparison of the number of bacterial colonies (CFU/ml) related to the infected hole in which the peptides nos. XII and XII were released from the carrier and acted against the infection, against the number of the colonies related to the infected hole which was filled only with the carrier alone.

In the hole in which the peptides were acting against *S. aureus* (Motol), the CFU/ml was $1.7 \times 10^3$, while in the hole filled with the carrier alone, the CFU/ml was $7.2 \times 10^7$. In the case of second graft bone infected with *S. epidermidis*, these values were $1 \times 10^2$ CFU/ml for the hole with the peptides and $3.7 \times 10^7$ CFU/ml for the hole without peptides. The used infected heads of the human hip joints were deactivated by autoclaving and then disposed as a biological waste in the Department of Pathology, University Hospital in Motol, Prague.

Example 9

Determination of Antifungal Effect of Peptides in Combination with Commonly Used Biocide ODDC on Yeast *Candida glabrata*

*C. glabrata* ATCC 2001 cells were aerobically cultivated at 30° C. on YPD medium (Formedium) overnight. A small volume of inoculum was added to fresh YPD medium to final concentration of cells $5 \times 10^6$ CFU/ml (corresponding value $OD_{600}=0.2$). Yeast cells were cultivated at 30° C. (190 rpm) until they reach early exponential growth phase, usually further 4-5 h. Cells were harvested, washed twice with distilled water (1.5 min, 3000 g) and resuspended in MES-TEA buffer (10 mM 4-morpholineethanesulphonic acid, pH 6.0 adjusted with triethanolamine, both chemicals from Sigma-Aldrich) to $OD_{600}=0.2$.

a) Determination of Immediate Effect of Peptides on Yeast Cells by Fluorescence diS-C$_3$(3) Probe The fluorescence probe diS-C$_3$(3) (3,3'-dipropylthiacarbocyanine iodide; Sigma-Aldrich) was added to a final concentration of $4 \times 10^{-8}$ mol.l$^{-1}$ to cell suspensions (3 ml). Fluorescence emission spectra of the cell suspensions were measured in spectroscopic cuvettes (Kartell) in an ISS PCI spectrofluorimeter. Fluorescence emission spectra were recorded in the range $\lambda_{em}$=560-590 nm, the excitation wavelength was $\lambda_{ex}$=531 nm. Scattered light was eliminated with an orange glass filter with a cutoff wavelength at 540 nm. Antimicrobial peptides and ODDC (octenidine dihydrochloride; Schülke & Mayr GmbH) were added to yeast suspensions after 10-20 min of staining. Optimization of this fluorescence method suitable for measurement of large amount of samples simultaneously in 96 well plates will be published soon.

Rate and extent of probe accumulation in cells, so called staining curve, records the dependence of the diS-C$_3$(3) fluorescence emission maximum wavelength $\lambda_{max}$ or intensity $I_{max}$, on the time of cell staining [Gášková et al., 1998].

The determination of the antifungal effect of tested compounds was based on comparison of staining curves of control cells (without addition of any compound) and cells affected by tested compound (peptide or ODDC or both), see FIG. 1A. Increased staining of cells exposed to the drug corresponded to their higher damage in short time.

b) Determination of Lethal Effect of Peptides on Yeast Cells by Plating Test

Figure 1B:
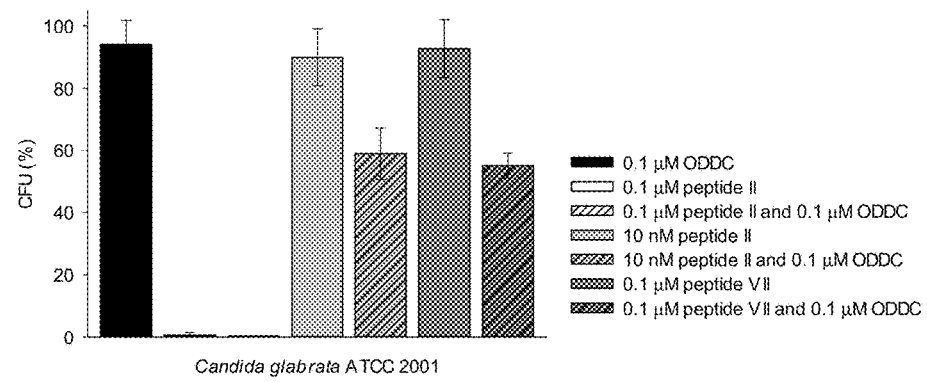

Cells from the early exponential growth phase were washed twice with sterile distilled water (1.5 min, 3000 g) and resuspended in MES-TEA buffer to $OD_{600}=0.2$. The cell suspension was divided into 1 ml aliquots in Eppendorf tubes. One sample served as a control, the tested compounds (peptides, ODDC) were added in selected concentrations to the rest of samples. Cells were incubated with drugs with occasional gentle stirring for 15 minutes, then 10 μl of cells were diluted 100-fold in distilled water and 15 μl aliquots were spread on 2% YPD agar (Formedium) plates (diameter of Petri plate 9 cm). The samples were always plated in triplicates. The number of colonies was determined after 24-h incubation of the plates at 30° C. The ratio of survived cells exposed to the tested compound in comparison to control sample (CFU) expressed in % gave evidence about lethal effect of tested compound on cells (inability to form colonies). The result of the plating test, which is shown in FIG. 1B, demonstrates high antifungal effect of peptide II, which is further amplified in combination with ODDC.

INDUSTRIAL APPLICABILITY

Practical application of antimicrobial peptides related to the hylanin will be profitable above all for the treatment of topical infections, both bacterial and yeast. Their use is for example expected in podiatry for the treatment of the wounds such as diabetic foot syndrome and/or leg ulcers, in orthopedics for the treatment of osteomyelitis (bone infection) where the topical use of antimicrobial peptides also involves their incorporation into local carriers used in orthopedics and prevention of the infection caused by bacterial biofilms formed on orthopedic implants. Furthermore, these peptides may be used in gynecology as a prescription against vaginal infection caused by yeast, for the treatment of the external ear canal infections (otitis externa), inflammation of eye conjunctiva (conjunctivitis acuta, conjunctivitis chronica), further for the treatment of chronic burn wound infections or combat wound infections, namely in the cases when the commonly used disinfectant or antibiotics fail owing to antimicrobial resistance. Such infections are hard to cure as they are in the majority of cases complicated by the occurrence of biofilms in which the microorganisms may be thousand times more resistant to antimicrobial compounds compared to their planktonic cells.

REFERENCES

1. Rulík M., Holá V., Růžička F., Votava M. a kolektiv: Mikrobiální biofilmy. Univerzita Palackého v Olomouci, Přírodovědecká fakulta, Olomouc 2011

2. Bjarnsholt T.: The role of bacterial biofilms in chronic infections. APMIS 121: 1-51 (2013)
3. Bjarnsholt T., Alhede M., Alhede M., Eickhardt-Sørensen S. R., Moser C., Kühl M., Jensen P. Ø., Høiby N.: The in vivo biofilm. Trends Microb. 21: 466-474 (2013)
4. Zasloff M.: Antimicrobial peptides of multicellular organisms. Nature 415, 389-395 (2002)
5. Hancock R. E. W., Sahl H.-G.: Antimicrobial and host-defense peptides as new anti-infective therapeutic strategies. Natur. Bitech. 24, 1551-1557 (2006)
6. Toke O.: Antimicrobial peptides: New candidates in the fight against bacteria infection. Biopolymers (Peptide Science) 80, 717-735 (2005)
7. Giuliani A., Pirri G., Nicoletto S. F.: Antimicrobial peptides: An overview of a promising class of therapeutics. Centr. Eur. J. Biol. 2, 1-33 (2007)
8. Zaiou M.: Multifunctional antimicrobial peptides: therapeutic targets in several human diseases. J. Mol. Med. 85, 317-329 (2007)
9. Oyston P. C. F, Fox M. A., Richards S. J., Clark G. C.: Novel peptide therapeutics for treatment of infections. J. Med. Microb. 58, 977-987 (2009)
10. Baltzer S. A, Brown M. H.: Antimicrobial peptides—promising alternatives to conventional antibiotics. J. Mol. Microbiol. Biotechnol. 20, 228-235 (2011)
11. Yeung A. T. Y., Gellatly S. L., Hancock R. E. W.: Multifunctional cationic host defence peptides and their clinical applications. Cell. Mol. Life. Sci. 68, 2161-2176 (2011)
12. Čeřovský V.: Antimikrobiální peptidy izolované z hmyzu. Chem. Listy 108, 344-353 (2014)
13. Otvos L. Jr.: Antimicrobial peptides isolated from insects. J. Peptide Sci. 6, 497-511 (2000)
14. Oren Z., Shai Y.: Mode of action of linear amphipathic α-helical antimicrobial peptides. Biopolymers 47, 451-463 (1998)
15. Yeaman M. R., Yount N. Y.: Mechanisms of antimicrobial peptide action and resistance. Pharm. Rev. 55, 27-55 (2003)
16. Nguyen L. T., Haney E. F., Vogel H. J.: The expanding scope of antimicrobial peptide structures and their modes of action. Trends Biotech. 29, 464-471 (2011)
17. Kuhn-Nentwig L.: Antimicrobial and cytolytic peptides of venomous arthropods. Cell. Mol. Life Sci. 60, 2651-2668 (2003)
18. Čeřovský V., Slaninová J., Fučík V., Hulačová H., Borovičková L., Ježek R., Bednárová L.: New potent antimicrobial peptides from the venom of Polistinae wasps and their analogs. Peptides 29, 992-1003 (2008)
19. Fields G. B, Noble R. L.: Solid phase peptide synthesis utilizing 9-fluorenylmethoxycarbonyl amino acid. Int. J. Pept. Protein Res. 35, 161-214 (1990)
20. Gášková D., Brodská B., Heřman P., Večeř J., Malínský J., Sigler K., Benada O., Plášek J.: Fluorescent probing of membrane potential in walled cells: diS-$C_3$(3) assay in *Saccharomyces cerevisiae*. Yeast 14, 1189-1197 (1998)

---

The invention claimed is:

1. An antimicrobial peptide selected from the group consisting of formulae I to XIX:

(I)
(SEQ ID NO. 3)
H-Gly-Ile-Met-Ser-Ser-Leu-Met-Lys-Lys-Leu-Lys-Lys-Ile-Ile-Ala-Lys-NH$_2$, (II),
(SEQ ID NO. 4)
H-*Gly-Ile-Met-Ser-Ser-Leu-Met-Lys-Lys-Leu-Lys-Lys-Ile-Ile-Ala-Lys*-NH$_2$, (III),
(SEQ ID NO. 5)
H-Gly-Ile-Leu-Ser-Ser-Leu-Leu-Lys-Lys-Leu-Lys-Lys-Ile-Ile-Ala-Lys-NH$_2$, (IV),
(SEQ ID NO. 6)
H-*Gly-Ile-Leu-Ser-Ser-Leu-Leu-Lys-Lys-Leu-Lys-Lys-Ile-Ile-Ala-Lys*-NH$_2$, (V),
(SEQ ID NO. 7)
H-Gly-Ile-Nle-Ser-Ser-Leu-Nle-Lys-Lys-Leu-Lys-Lys-Ile-Ile-Ala-Lys-NH$_2$, (VI),
(SEQ ID NO. 8)
H-*Lys*-Ile-Leu-Ser-Ser-Leu-Leu-Lys-Lys-Leu-Lys-Lys-Ile-Ile-Ala-Lys-NH$_2$, (VII),
(SEQ ID NO. 9)
H-Gly-Ile-Met-Ser-Ser-Leu-Met-Lys-Lys-Leu-Lys-Lys-Ile-Ile-Lys-Lys-NH$_2$, (VIII),
(SEQ ID NO. 10)
H-Gly-Ile-Met-Ser-Ser-Leu-Met-Lys-Lys-Leu-Ala-Ala-His-Ile-Lys-Lys-NH$_2$, (IX),
(SEQ ID NO. 11)
H-Gly-Ile-Met-Ser-Ser-Leu-Met-Lys-Lys-Leu-Ala-Ala-Ile-Ile-Lys-Lys-NH$_2$, (X),
(SEQ ID NO. 12)
H-Gly-Ile-Leu-Lys-Ser-Leu-Leu-Lys-Lys-Leu-Lys-Lys-Ile-Ile-Ala-Lys-NH$_2$, (XI),
(SEQ ID NO. 13)
H-Gly-Ile-Leu-Ser-Lys-Leu-Leu-Lys-Lys-Leu-Lys-Lys-Ile-Ile-Ala-Lys-NH$_2$,

-continued (XII),
(SEQ ID NO. 14)
H-Gly-Ile-Leu-Ser-Ser-Leu-Trp-Lys-Lys-Leu-Lys-Lys-Ile-Ile-Ala-Lys-NH₂, (XIII),
(SEQ ID NO. 15)
H-*Gly-Ile-Leu-Ser-Ser-Leu-Trp-Lys-Lys-Leu-Lys-Lys-Ile-Ile-Ala-Lys*-NH₂, (XIV),
(SEQ ID NO. 16)
H-Gly-Ile-Trp-Ser-Ser-Leu-Leu-Lys-Lys-Leu-Lys-Lys-Ile-Ile-Ala-Lys-NH₂, (XV),
(SEQ ID NO. 17)
H-Gly-Ile-Leu-Ser-Ser-Trp-Leu-Lys-Lys-Leu-Lys-Lys-Ile-Ile-Ala-Lys-NH₂, (XVI),
(SEQ ID NO. 18)
H-Gly-Ile-Leu-Ser-Ser-Leu-Leu-Lys-Lys-Trp-Lys-Lys-Ile-Ile-Ala-Lys-NH₂, (XVII),
(SEQ ID NO. 19)
H-Gly-Ile-Leu-Ser-Ser-Leu-Trp-Lys-Lys-Leu-Lys-Lys-Trp-Ile-Ala-Lys-NH₂, (XVIII),
(SEQ ID NO. 20)
H-Gly-Ile-Leu-Ser-Ser-Leu-Leu-Lys-Lys-Leu-Lys-Lys-Trp-Ile-Ala-Lys-NH₂,
and (XIX),
(SEQ ID NO. 21)
H-Gly-Ile-Leu-Ser-Ser-Leu-Trp-Lys-Lys-Leu-Lys-Lys-Ile-Ile-Ala-*Lys*-NH₂, where amino acids in the D configuration are shown in italics.

2. A pharmaceutical composition for use in the treatment or prevention of a topical infection comprising a therapeutically effective amount of at least one of the peptides of formulae I to XIX of claim 1, wherein the topical infection is selected from the group consisting of difficult-to-heal wounds and skin disorders, mucosal infections, infectious diseases of bone and surrounding tissues, and infections that are caused by the formation of microbial biofilms.

3. A pharmaceutical composition for use in the prevention or elimination of an infectious agent from catheters, and joint and bone replacement orthopedics and cements, and for the prevention of infection from orthopedic implants comprising a therapeutically effective amount of at least one of the peptides of formulae I to XIX of claim 1.

4. A pharmaceutical composition for use in the augmentation of the effect of locally acting antibacterial drugs and wound dressings during the treatment of topical infections comprising a therapeutically effective amount of at least one of the peptides of formulae I to XIX of claim 1.

5. A composition for incorporation into local carriers used in orthopedics comprising at least one of the peptides of formulae I to XIX of claim 1, and a second ingredient selected from the group consisting of calcium phosphate, calcium sulphate, bioactive glass, apatite/wollastonite bioactive glass-ceramics, hydrogels, collagen, bone grafts, bone cement, synthetic polymers made from polymethylmethacrylate, copolymer of polymethylmethacrylate and hydroxypolymethylmethacrylate, polyanhydride, polylactide, polyglycolide, copolymers of hydroxybutyrate, hydroxyvalerate, polyhydroxyalkanoate, polycaprolactone, glycerol gelatin sponge, and composites made of polymers and inorganic carriers.

6. A pharmaceutical composition comprising a therapeutically effective amount of at least one the peptides of formulae I to XIX according to claim 1, a second active ingredient, which is an antibiotic or antifungal agent and/or a disinfecting agent, optionally also at least one pharmaceutically acceptable wound dressing, carrier, filling material and/or diluent.

7. A pharmaceutical composition according to claim 6 for use in the treatment or prevention of infections that are caused by the formation of microbial biofilms.

8. A pharmaceutical composition according to claim 6 for use in the treatment or prevention of topical infections chosen from the group consisting of difficult-to-heal wounds and skin disorders, mucosal infection, infectious diseases of the bone and surrounding tissues, infectious complications after implantation of joint replacements and after osteosynthesis, and infections that are caused by the formation of microbial biofilms.

9. A disinfectant comprising at least one of the peptides of formulae I to XIX according to claim 1.

* * * * *

SEQUENCE LISTING

```
<160> NUMBER OF SEQ ID NOS: 21

<210> SEQ ID NO 1
<211> LENGTH: 16
<212> TYPE: PRT
<213> ORGANISM: Hylaeus signatus

<400> SEQUENCE: 1

Gly Ile Met Ser Ser Leu Met Lys Lys Leu Ala Ala His Ile Ala Lys
1               5                   10                  15

<210> SEQ ID NO 2
<211> LENGTH: 16
<212> TYPE: PRT
<213> ORGANISM: Artificial
<220> FEATURE:
<223> OTHER INFORMATION: Artificial antimicrobial peptide
<220> FEATURE:
<221> NAME/KEY: VARIANT
<222> LOCATION: (1)..(1)
<223> OTHER INFORMATION: Gly or Lys or bAla
<220> FEATURE:
<221> NAME/KEY: VARIANT
<222> LOCATION: (3)..(3)
<223> OTHER INFORMATION: Met or Leu or Nle or Ile or Trp or Val or Phe
<220> FEATURE:
<221> NAME/KEY: VARIANT
<222> LOCATION: (4)..(4)
<223> OTHER INFORMATION: Ser or Lys or Arg or Orn
<220> FEATURE:
<221> NAME/KEY: VARIANT
<222> LOCATION: (5)..(5)
<223> OTHER INFORMATION: Ser or Lys or Arg or Orn
<220> FEATURE:
<221> NAME/KEY: VARIANT
<222> LOCATION: (6)..(6)
<223> OTHER INFORMATION: Leu or Nle or Ile or Trp or Val or Phe
<220> FEATURE:
<221> NAME/KEY: VARIANT
<222> LOCATION: (7)..(7)
```

```
<223> OTHER INFORMATION: Met or Leu or Nle or Ile or Trp or Val or Phe
<220> FEATURE:
<221> NAME/KEY: VARIANT
<222> LOCATION: (10)..(10)
<223> OTHER INFORMATION: Leu or Nle or Ile or Trp
<220> FEATURE:
<221> NAME/KEY: VARIANT
<222> LOCATION: (11)..(11)
<223> OTHER INFORMATION: Lys or Arg or Orn or Ala
<220> FEATURE:
<221> NAME/KEY: VARIANT
<222> LOCATION: (12)..(12)
<223> OTHER INFORMATION: Lys or Arg or Orn or Ala
<220> FEATURE:
<221> NAME/KEY: VARIANT
<222> LOCATION: (13)..(13)
<223> OTHER INFORMATION: Ile or Leu or Nle or His
<220> FEATURE:
<221> NAME/KEY: VARIANT
<222> LOCATION: (15)..(15)
<223> OTHER INFORMATION: Lys or Arg or Orn or Ala

<400> SEQUENCE: 2

Xaa Ile Xaa Xaa Xaa Xaa Xaa Lys Lys Xaa Xaa Xaa Xaa Ile Xaa Lys
1               5                  10                  15

<210> SEQ ID NO 3
<211> LENGTH: 16
<212> TYPE: PRT
<213> ORGANISM: Artificial
<220> FEATURE:
<223> OTHER INFORMATION: Peptide of formula I

<400> SEQUENCE: 3

Gly Ile Met Ser Ser Leu Met Lys Lys Leu Lys Lys Ile Ile Ala Lys
1               5                  10                  15

<210> SEQ ID NO 4
<211> LENGTH: 16
<212> TYPE: PRT
<213> ORGANISM: Artificial
<220> FEATURE:
<223> OTHER INFORMATION: Peptide of formula II

<400> SEQUENCE: 4

Gly Ile Met Ser Ser Leu Met Lys Lys Leu Lys Lys Ile Ile Ala Lys
1               5                  10                  15

<210> SEQ ID NO 5
<211> LENGTH: 16
<212> TYPE: PRT
<213> ORGANISM: Artificial
<220> FEATURE:
<223> OTHER INFORMATION: Peptide of formula III

<400> SEQUENCE: 5

Gly Ile Leu Ser Ser Leu Leu Lys Lys Leu Lys Lys Ile Ile Ala Lys
1               5                  10                  15

<210> SEQ ID NO 6
<211> LENGTH: 16
<212> TYPE: PRT
<213> ORGANISM: Artificial
<220> FEATURE:
<223> OTHER INFORMATION: Peptide of formula IV

<400> SEQUENCE: 6

Gly Ile Leu Ser Ser Leu Leu Lys Lys Leu Lys Lys Ile Ile Ala Lys
1               5                  10                  15
```

```
<210> SEQ ID NO 7
<211> LENGTH: 16
<212> TYPE: PRT
<213> ORGANISM: Artificial
<220> FEATURE:
<223> OTHER INFORMATION: Peptide of formula V
<220> FEATURE:
<221> NAME/KEY: VARIANT
<222> LOCATION: (3)..(3)
<223> OTHER INFORMATION: Nle
<220> FEATURE:
<221> NAME/KEY: VARIANT
<222> LOCATION: (7)..(7)
<223> OTHER INFORMATION: Nle

<400> SEQUENCE: 7

Gly Ile Xaa Ser Ser Leu Xaa Lys Lys Leu Lys Lys Ile Ile Ala Lys
1               5                   10                  15

<210> SEQ ID NO 8
<211> LENGTH: 16
<212> TYPE: PRT
<213> ORGANISM: Artificial
<220> FEATURE:
<223> OTHER INFORMATION: Peptide of formula VI

<400> SEQUENCE: 8

Lys Ile Leu Ser Ser Leu Leu Lys Lys Leu Lys Lys Ile Ile Ala Lys
1               5                   10                  15

<210> SEQ ID NO 9
<211> LENGTH: 16
<212> TYPE: PRT
<213> ORGANISM: Artificial
<220> FEATURE:
<223> OTHER INFORMATION: Peptide of formula VII

<400> SEQUENCE: 9

Gly Ile Met Ser Ser Leu Met Lys Lys Leu Lys Lys Ile Ile Lys Lys
1               5                   10                  15

<210> SEQ ID NO 10
<211> LENGTH: 16
<212> TYPE: PRT
<213> ORGANISM: Artificial
<220> FEATURE:
<223> OTHER INFORMATION: Peptide of formula VIII

<400> SEQUENCE: 10

Gly Ile Met Ser Ser Leu Met Lys Lys Leu Ala Ala His Ile Lys Lys
1               5                   10                  15

<210> SEQ ID NO 11
<211> LENGTH: 16
<212> TYPE: PRT
<213> ORGANISM: Artificial
<220> FEATURE:
<223> OTHER INFORMATION: Peptide of formula IX

<400> SEQUENCE: 11

Gly Ile Met Ser Ser Leu Met Lys Lys Leu Ala Ala Ile Ile Lys Lys
1               5                   10                  15

<210> SEQ ID NO 12
<211> LENGTH: 16
<212> TYPE: PRT
<213> ORGANISM: Artificial
<220> FEATURE:
```

-continued

```
<223> OTHER INFORMATION: Peptide of formula X

<400> SEQUENCE: 12

Gly Ile Leu Lys Ser Leu Leu Lys Lys Leu Lys Lys Ile Ile Ala Lys
1               5                   10                  15

<210> SEQ ID NO 13
<211> LENGTH: 16
<212> TYPE: PRT
<213> ORGANISM: Artificial
<220> FEATURE:
<223> OTHER INFORMATION: Peptide of formula XI

<400> SEQUENCE: 13

Gly Ile Leu Ser Lys Leu Leu Lys Lys Leu Lys Lys Ile Ile Ala Lys
1               5                   10                  15

<210> SEQ ID NO 14
<211> LENGTH: 16
<212> TYPE: PRT
<213> ORGANISM: Artificial
<220> FEATURE:
<223> OTHER INFORMATION: Peptide of formula XII

<400> SEQUENCE: 14

Gly Ile Leu Ser Ser Leu Trp Lys Lys Leu Lys Lys Ile Ile Ala Lys
1               5                   10                  15

<210> SEQ ID NO 15
<211> LENGTH: 16
<212> TYPE: PRT
<213> ORGANISM: Artificial
<220> FEATURE:
<223> OTHER INFORMATION: Peptide of formula XIII

<400> SEQUENCE: 15

Gly Ile Leu Ser Ser Leu Trp Lys Lys Leu Lys Lys Ile Ile Ala Lys
1               5                   10                  15

<210> SEQ ID NO 16
<211> LENGTH: 16
<212> TYPE: PRT
<213> ORGANISM: Artificial
<220> FEATURE:
<223> OTHER INFORMATION: Peptide of formula XIV

<400> SEQUENCE: 16

Gly Ile Trp Ser Ser Leu Leu Lys Lys Leu Lys Lys Ile Ile Ala Lys
1               5                   10                  15

<210> SEQ ID NO 17
<211> LENGTH: 16
<212> TYPE: PRT
<213> ORGANISM: Artificial
<220> FEATURE:
<223> OTHER INFORMATION: Peptide of formula XV

<400> SEQUENCE: 17

Gly Ile Leu Ser Ser Trp Leu Lys Lys Leu Lys Lys Ile Ile Ala Lys
1               5                   10                  15

<210> SEQ ID NO 18
<211> LENGTH: 16
<212> TYPE: PRT
<213> ORGANISM: Artificial
<220> FEATURE:
<223> OTHER INFORMATION: Peptide of formula XVI
```

```
<400> SEQUENCE: 18

Gly Ile Leu Ser Ser Leu Leu Lys Lys Trp Lys Lys Ile Ile Ala Lys
1               5                   10                  15

<210> SEQ ID NO 19
<211> LENGTH: 16
<212> TYPE: PRT
<213> ORGANISM: Artificial
<220> FEATURE:
<223> OTHER INFORMATION: Peptide of formula XVII

<400> SEQUENCE: 19

Gly Ile Leu Ser Ser Leu Trp Lys Lys Leu Lys Lys Trp Ile Ala Lys
1               5                   10                  15

<210> SEQ ID NO 20
<211> LENGTH: 16
<212> TYPE: PRT
<213> ORGANISM: Artificial
<220> FEATURE:
<223> OTHER INFORMATION: Peptide of formula XVIII

<400> SEQUENCE: 20

Gly Ile Leu Ser Ser Leu Leu Lys Lys Leu Lys Lys Trp Ile Ala Lys
1               5                   10                  15

<210> SEQ ID NO 21
<211> LENGTH: 16
<212> TYPE: PRT
<213> ORGANISM: Artificial
<220> FEATURE:
<223> OTHER INFORMATION: Peptide of formula XIX

<400> SEQUENCE: 21

Gly Ile Leu Ser Ser Leu Trp Lys Lys Leu Lys Lys Ile Ile Ala Lys
1               5                   10                  15
```